United States Patent
Gottstein et al.

(10) Patent No.: US 11,622,952 B2
(45) Date of Patent: Apr. 11, 2023

(54) TABLETS WITH HIGH ACTIVE INGREDIENT CONTENT OF OMEGA-3 FATTY ACID AMINO ACID SALTS

(71) Applicant: Evonik Operations GmbH, Essen (DE)

(72) Inventors: Thomas Gottstein, Babenhausen (DE); Michael Schwarm, Alzenau (DE); Guenter Knaup, Hanau (DE)

(73) Assignee: Evonik Operations GmbH, Essen (DE)

( * ) Notice: Subject to any disclaimer, the term of this patent is extended or adjusted under 35 U.S.C. 154(b) by 121 days.

(21) Appl. No.: 16/638,533

(22) PCT Filed: Aug. 15, 2018

(86) PCT No.: PCT/EP2018/072138
§ 371 (c)(1),
(2) Date: Feb. 12, 2020

(87) PCT Pub. No.: WO2019/034698
PCT Pub. Date: Feb. 21, 2019

(65) Prior Publication Data
US 2021/0121429 A1    Apr. 29, 2021

(30) Foreign Application Priority Data

Aug. 15, 2017 (EP) .................... 17186305

(51) Int. Cl.
| | | |
|---|---|---|
| *A61K 31/202* | (2006.01) | |
| *A23L 33/12* | (2016.01) | |
| *A23L 33/175* | (2016.01) | |
| *A61K 9/20* | (2006.01) | |
| *A61K 31/198* | (2006.01) | |

(52) U.S. Cl.
CPC ............ *A61K 31/202* (2013.01); *A23L 33/12* (2016.08); *A23L 33/175* (2016.08); *A61K 9/2013* (2013.01); *A61K 31/198* (2013.01)

(58) Field of Classification Search
CPC ... A61K 31/202; A61K 31/198; A61K 9/2013
See application file for complete search history.

(56) References Cited

U.S. PATENT DOCUMENTS

| | | |
|---|---|---|
| 2009/0017118 A1 | 1/2009 | Samuelsen et al. |
| 2012/0231077 A1 | 9/2012 | Samuelsen et al. |
| 2017/0119841 A1* | 5/2017 | Mathias ............ C07K 5/06069 |
| 2017/0367394 A1 | 12/2017 | Knaup et al. |

FOREIGN PATENT DOCUMENTS

| | | |
|---|---|---|
| GB | 2 216 522 A | 10/1989 |
| WO | WO 2016/102316 A1 | 6/2016 |

OTHER PUBLICATIONS

Porter et al., "An evaluation of the properties of enteric coating polymers: measurement of glass transition temperature", Journal of Pharmacy and Pharmacology, vol. 35, No. 6, pp. 341-344 (1983).*
International Search Report and Written Opinion dated Dec. 19, 2018 in PCT/EP2018/072138 filed on Aug. 15, 2018.
Gala et al., "Pharmaceutical Applications of Eutectic Mixtures", Journal of Developing Drugs, vol. 2, No. 3, 2013, pp. 1-2, XP055445411.
Matsumoto et al., "Impact of compression pressure on tablet appearance", International Journal of Pharmaceutics, Elsevier, vol. 341, 2007, pp. 44-49, XP022166286.
Siddiqui et al., "Measurement of surface color as an expedient QC method for the detection of deviations in tablet hardness", International Journal of Pharmaceutics, Elsevier, vol. 341, 2007, pp. 173-180, XP022166301.
Combined Chinese Office Action and Search Report dated Aug. 2, 2022 in Chinese Patent Application No. 201880052754.8 (with English abstract), 13 pages.

* cited by examiner

*Primary Examiner* — Kevin E Weddington
(74) *Attorney, Agent, or Firm* — Oblon, McClelland, Maier & Neustadt, L.L.P.

(57) ABSTRACT

The present invention relates to a tablet comprising one or more omega-3 fatty acid amino acid salts, a method for preparing a tablet according to the invention and the use of a tablet according to the invention as a food supplement or as a pharmaceutical product.

19 Claims, 2 Drawing Sheets

Figure 1: Work during compression, analysis of force-path data
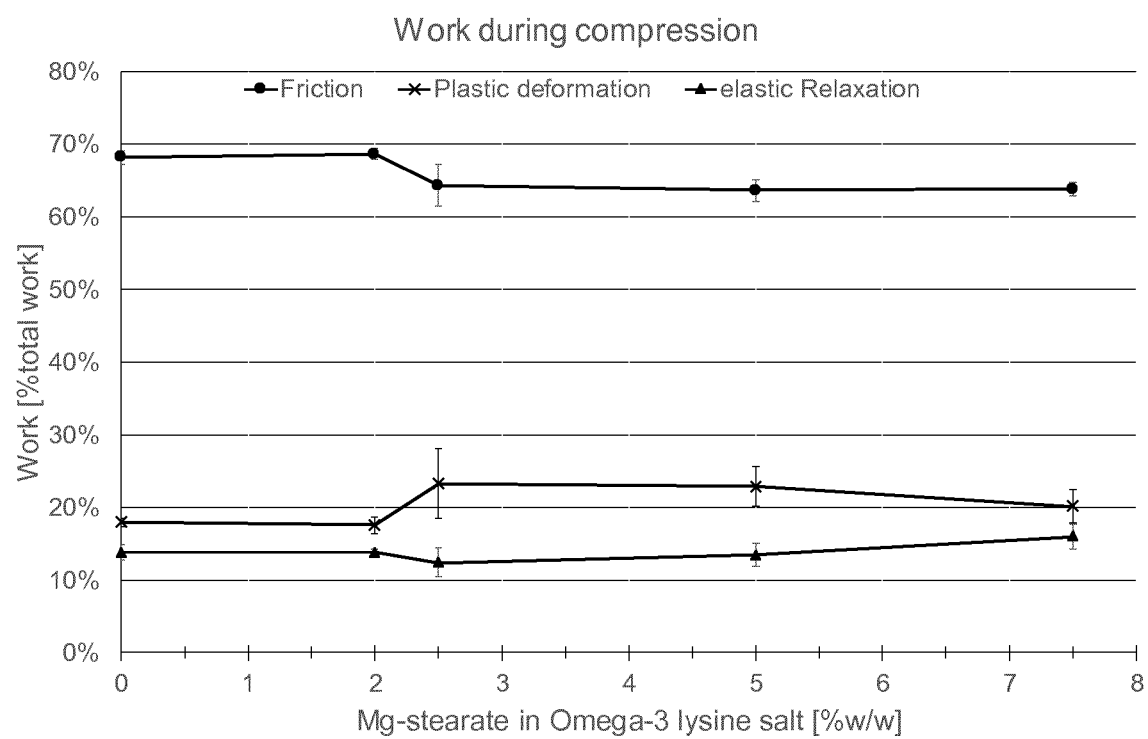

Figure 2: Color change during compression
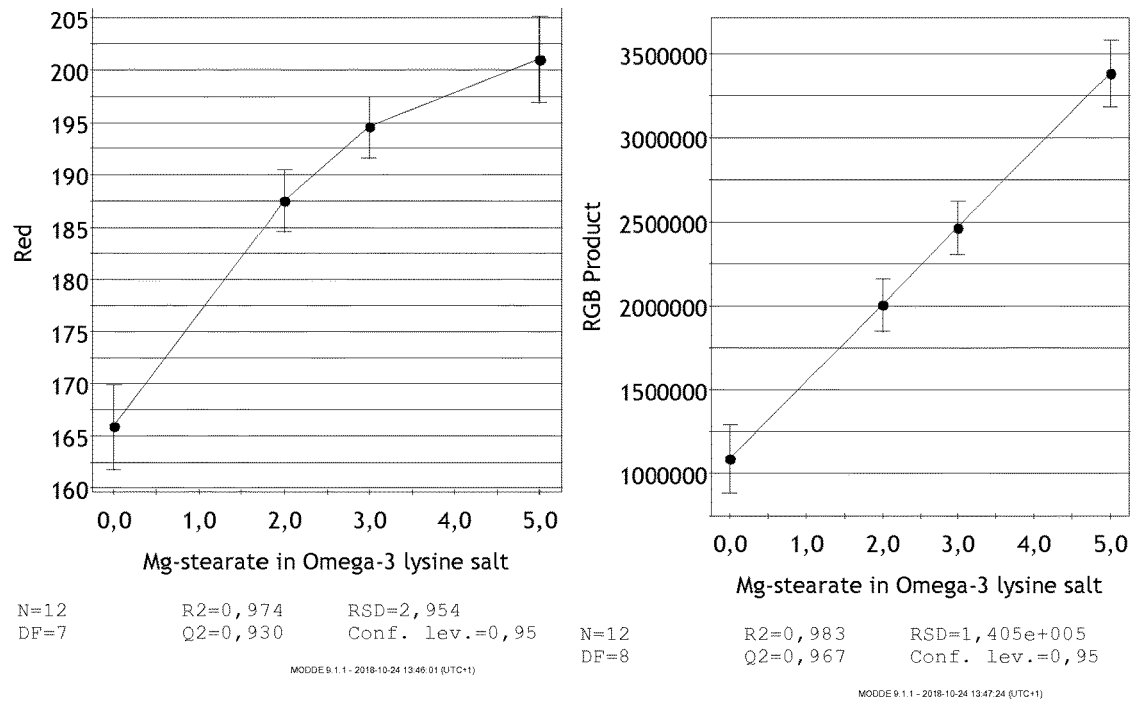
a)
b)
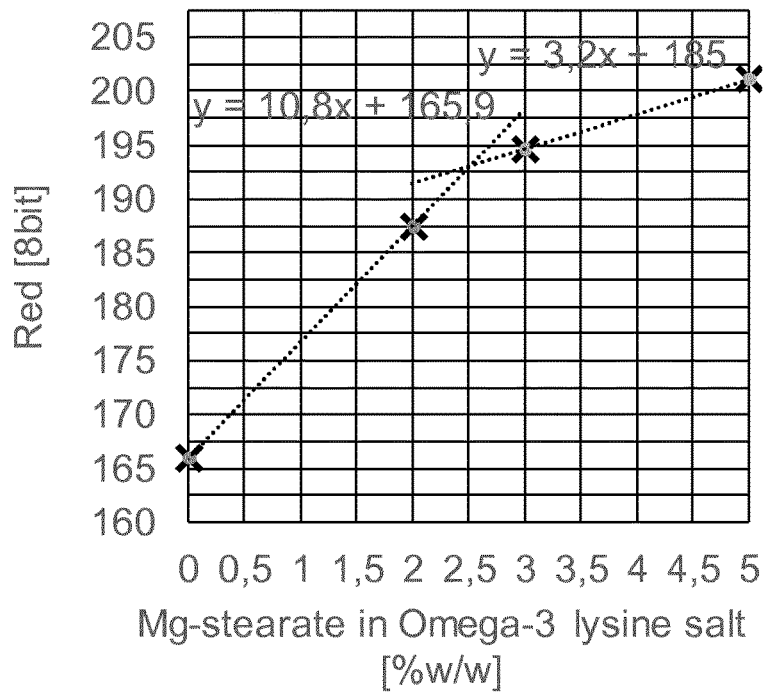
c)

TABLETS WITH HIGH ACTIVE INGREDIENT CONTENT OF OMEGA-3 FATTY ACID AMINO ACID SALTS

BACKGROUND

Omega-3 fatty acids, particularly eicosapentaenoic acid (EPA) and docosahexaenoic acid (DHA), are linked to numerous positive health effects on the cardiovascular system, on inflammatory disorders, on brain development and function, on disruptions of the central nervous system and on other areas (C. H. S. Ruxton, S. C. Reed, M. J. A. Simpson, K. J. Millington, J. Hum. Nutr. Dietet 2004, 17, 449). Therefore, the intake of omega-3 fatty acids is supported by statements of regulatory agencies. For instance, the EFSA (European Food Safety Authority) recommends for adults a daily intake of 250 mg of EPA+DHA (EFSA Panel on Dietetic Products, Nutrition and Allergies, EFSA Journal 2010, 8 (3), 1461). The AHA (American Heart Association) advises the intake of at least two meals of fatty fish per week for persons without documented cardiovascular disorders, the intake of about 1 g of EPA+DHA per day from fish or food supplements for persons with documented cardiovascular disorders and the intake of 2-4 g of EPA+DHA per day for the treatment of raised blood lipid values (P. M. Kris-Etherton, W. S. Harris, L. J. Appel, Circulation 2002, 106, 2747). Moreover, the authorities have expressly approved health claims for omega-3 fatty acids determined on the basis of clinical studies (EU Register on Nutrition and Health Claims; see also: EFSA Journal 2011, 9 (4), 2078). Therefore, omega-3 fatty acids, especially from fish oil but also from other plant or microbial sources, are increasingly used as food supplements, food additives and medicaments.

According to standard nomenclature, polyunsaturated fatty acids are classified according to the number and position of the double bonds. There are two series or families, depending on the position of the double bond which is closest to the methyl end of the fatty acid. The omega-3 series comprises a double bond at the third carbon atom whereas the omega-6 series has no double bond up to the sixth carbon atom. Thus, docosahexaenoic acid (DHA) has a chain length of 22 carbon atoms with 6 double bonds beginning with the third carbon atom from the methyl end and is referred to as "22:6 n-3" (all-cis-4,7,10,13,16,19-docosahexaenoic acid). Another important omega-3 fatty acid is eicosapentaenoic acid (EPA), which is referred to as "20:5 n-3" (all-cis-5,8,11,14,17-eicosapentaenoic acid).

Most of the omega-3 fatty acid products introduced to the market are offered in the form of oils, starting from fish oil with a content of about 30% omega-3 fatty acids up to concentrates with over 90% content of EPA or DHA or mixtures of these two omega-3 fatty acids. The formulations used are predominantly soft gelatine capsules. In addition, numerous further product forms have been described, such as microencapsulations or powder preparations (C. J. Barrow, B. Wang, B. Adhikari, H. Liu, Spray drying and encapsulation of omega-3 oils, in: Food enrichment with omega-3 fatty acids (Eds.: C. Jacobsen, N. S. Nielsen, A. Frisenfeldt Horn, A.-D. Moltke Soerensen), pp. 194-225, Woodhead Publishing Ltd., Cambridge 2013, ISBN 978-0-85709-428-5; T.-L. Torgersen, J. Klaveness, A. H. Myrset, US 2012/0156296 A1). Chemically, these are usually triglycerides or fatty acid ethyl esters with various concentrations of omega-3 fatty acids, while phospholipids, e.g. as krill oil, free fatty acids (T. J. Maines, B. N. M. Machielse, B. M. Mehta, G. L. Wisler, M. H. Davidson, P. R. Wood, US 2013/0209556 A1; M. H. Davidson, G. H. Wisler, US 2013/0095179 A1; N. J. Duragkar, US 2014/0018558 A1; N. J. Duragkar, US 2014/0051877 A1) and various salts of fatty acids are also known, e.g. with potassium, sodium, ammonium (H. J. Hsu, S. Trusovs, T. Popova, U.S. Pat. No. 8,203,013 B2), calcium and magnesium, (J. A. Kralovec, H. S. Ewart, J. H. D. Wright, L. V. Watson, D. Dennis, C. J. Barrow, J. Functional Foods 2009, 1, 217; G. K. Strohmaier, N. D. Luchini, M. A. Varcho, E. D. Frederiksen, U.S. Pat. No. 7,098,352 B2), which are not water-soluble, aminoalcohols (P. Rongved, J. Klaveness, US 2007/0213298 A1), amine compounds such as piperazine (B. L. Mylari, F. C. Sciavolino, US 2014/0011814 A1), and guanidine compounds such as metformin (M. Manku, J. Rowe, US 2012/0093922 A1; B. L. Mylari, F. C. Sciavolino, US 2012/0178813 A1; B. L. Mylari, F. C. Sciavolino, US 2013/0281535 A1; B. L. Mylari, F. C. Sciavolino, WO 2014/011895 A2). The bioavailability of the different omega-3 derivatives for the human body is very diverse. Since omega-3 fatty acids as free fatty acids together with monoacyl glycerides are absorbed in the small intestine, the bioavailability of free omega-3 fatty acids is better than that of triglycerides or ethyl esters since these have firstly to be cleaved to the free fatty acids in the digestive tract (J. P. Schuchhardt, A. Hahn, Prostaglandins Leukotrienes Essent. Fatty Acids 2013, 89, 1). The stability to oxidation is also very different for different omega-3 derivatives. Free omega-3 fatty acids are described as very sensitive to oxidation (J. P. Schuchhardt, A. Hahn, Prostaglandins Leukotrienes Essent. Fatty Acids 2013, 89, 1). For the use of a solid omega-3 form, an increased stability compared to liquid products is assumed (J. A. Kralovec, H. S. Ewart, J. H. D. Wright, L. V. Watson, D. Dennis, C. J. Barrow, J. Functional Foods 2009, 1, 217).

Furthermore, preparations of omega-3 fatty acids with diverse amino acids, such as lysine and arginine, are known, either as mixtures (P. Literati Nagy, M. Boros, J. Szilbereky, I. Racz, G. Soos, M. Koller, A. Pinter, G. Nemeth, D E 3907649 A1) or as salts (B. L. Mylari, F. C. Sciavolino, WO 2014/011895 A1; T. Bruzzese, EP 0699437 A1; T. Bruzzese, EP0734373 B1; T. Bruzzese, U.S. Pat. No. 5,750,572, J. Torras et al., Nephron 1994, 67, 66; J. Torras et al., Nephron 1995, 69, 318; J. Torras et al., Transplantation Proc. 1992, 24 (6), 2583; S. El Boustani et al., Lipids 1987, 22 (10), 711; H. Shibuya, US 2003/0100610 A1). The preparation of omega-3 aminoalcohol salts by spray-drying is also mentioned (P. Rongved, J. Klaveness, US 2007/0213298 A1). In a general form, the preparation of DHA amino acid salts is described by evaporation to dryness under high vacuum and low temperature or freeze-drying (T. Bruzzese, EP0734373 B1 and U.S. Pat. No. 5,750,572). The resulting products are described as very thick, transparent oils, which transform at low temperature into solids of waxy appearance and consistency.

Finally, processing of omega-3 amino acid preparations to tablets is known in principle. The concentrations of omega-3 fatty acids in the finished tablets, owing to the presence of amino acids in the preparations and the additional use of auxiliaries such as binders, release agents and structure-forming substances, is at most 38% in the case of omega-3 amino acid salts (T. Bruzzese, EP0734373 B1 and U.S. Pat. No. 5,750,572, Example 15), or at most 34.6% in the case of omega-3 fatty acid amino acid mixtures (P. Literati Nagy, M. Boros, J. Szilbereky, I. Racz, G. Soos, M. Koller, A. Pinter, G. Nemeth, D E 3907649 A1), according to the formulae mentioned in the examples. The coating of omega-3 softgel capsules with an enteric coating is also described.

However, despite the extensive prior art, all the known product forms have one or more disadvantages such that further improvement needs exist. For instance, the most common omega-3 triglyceride and ethyl ester oils are inherently less readily bioavailable than the free omega-3 fatty acids. These are in turn particularly sensitive to oxidation. The established formulation as a soft gelatine capsule is more complicated, more expensive and more prone to defects than a simple tabletting of a solid. In addition, many consumers oppose the consumption of gelatine of animal origin on religious or other grounds. Solid omega-3 formulations described to date, either as microencapsulated or bound oil, as mixtures with amino acids or as salts, have other serious disadvantages. For instance, alkali metal salts are strongly alkaline in aqueous solution whereas alkaline earth metal salts are practically water-insoluble which limits the bioavailability. Although mixtures or salts with amino acids are soluble and should therefore be readily bioavailable, the tablets described still have relatively low omega-3 fatty acid contents of at most 38% for salts of omega-3 fatty acids and amino acids and at most 34.6% for mixtures of omega-3 fatty acids and amino acids. This relies on large amounts of added auxiliaries such as release agents and binders and structure-forming substances which are used for the preparation of a stable tablet. The low omega-3 fatty acid contents lead however to the fact that the consumer must take the corresponding products frequently and in relatively large amounts in order to reach the recommended daily intake amounts, which may be several 100 milligrams up to a few grams per day depending on the country and health condition.

Due to the disadvantages described, a need exists for solid omega-3 fatty acid preparations which can be readily and cost-effectively formulated as tablets, which have better bioavailability and in addition are also more stable than standard liquid formulations, and which in addition are as highly concentrated in omega-3 fatty acids as possible in order to keep the daily intake amount as low as possible.

Under normal conditions, pure omega-3 amino acid salts are not compressible to a tablet. The cohesion of the mixture is not sufficient to avoid disrupture of the tablet when it is removed from the mould. Applying a higher pressure during compression causes destruction of the tablet (due to excess compression). Therefore, there exists a need to provide compositions containing high amounts of omega-3 fatty acid salts, which can directly be compressed to tablets without the need of high amounts of excipients in the composition.

It has now been found, surprisingly, that tablets comprising a composition containing one or more omega-3 fatty acid amino acid salts are compressible, when the composition has a glass transition temperature Tg of <110° C., preferably <100° C.

SUMMARY

According to the present invention, the composition, which shall be compressed to a tablet is softened to improve cohesion of the composition. The cohesion of the composition is improved by lowering its glass transition temperature under the critical value. It has now surprisingly been found that by reduction of the glass transition temperature below 110° C. tabletting of omega-3 amino acid salts is possible without the need of further additives.

The present invention accordingly relates in a first aspect to a tablet comprising a composition containing one or more omega-3 fatty acid amino acid salts, characterized in that the amino acid is chosen from basic amino acids, preferably lysine, arginine, ornithine, histidine, citrulline and mixtures of the same and the composition has a glass transition temperature Tg of <110° C., preferably <100° C.

brief DESCRIPTION OF DRAWINGS

FIG. 1 shows work during compression depending on Mg-stearate contents, divided into friction, deformation and elastic relaxation (Example 2).

FIG. 2 shows color change during compression (Example 3). (a) and (c) show red-values for different Mg-stearate contents during compression. (b) shows RCSB-products for different Mg-stearate contents during compression.

DETAILED DESCRIPTION

The glass-transition temperature Tg of a material characterizes the range of temperatures over which this glass transition occurs. It is always lower than the melting temperature, Tm, of the crystalline state of the material, if one exists. The glass transition is the reversible transition in amorphous materials (or in amorphous regions within semicrystalline materials) from a hard and relatively brittle "glassy" state into a viscous or rubbery state as the temperature is increased.

In a further preferred embodiment of the present invention the glass-transition temperature Tg is reduced to values below 90° C., preferably below 80° C., more preferably below 70° C.

In an alternative embodiment, the composition contains at least one substance, which forms a eutectic system with the omega-3 fatty acid amino acid salts and thereby acts as a plasticizer. It is preferred that the content of the plasticizer is at least 2% by weight, preferably at least 2.5% by weight, more preferably at least 3% by weight, based on the total amount of omega-3 fatty acid amino acid salts in the composition.

It was a surprising finding that substances, which form a eutectic system with omega-3 fatty acid amino acid salts can act as plasticizer.

In an advantageous configuration, the plasticizer is selected from fatty acids, fatty acid salts, fatty acid esters and polyethylene glycol, preferably magnesium stearate, stearic acid, sodium stearyl fumarate, zinc stearate, calcium stearate, glyceryl palmitostearate, glycerol behenate, glyceryl monostearate, sodium benzoate, sodium lauryl sulfate, sorbitan monostearate, sucrose monopalmitate and polyethylenglycol (MW>1500 g/mol).

Normally, these substances are used as lubricant and completely prevent compression when applied in concentrations above 3% by weight, based on the total weight of the composition. In general, these substances are used in maximal amounts of 0.5 to 1% by weight, based on the total weight of the composition. Magnesium stearate for example is often used as an anti-adherent in the manufacture of medical tablets, capsules and powders in amounts ranging between 0.5 and 1% by weight, based on the total weight of the composition. In this regard, the substance is also useful because it has lubricating properties, preventing ingredients from sticking to manufacturing equipment during the compression of powder compositions into solid tablets. In fact, magnesium stearate is the most commonly used lubricant for tablets.

It has now surprisingly been found that lubricants, such as magnesium stearate work as plasticizers when they are used in the amounts described according to the present invention and make tableting possible, even at high concentrations of 70:30 omega-3 amino acid salts to magnesium stearate.

Due to the compressibility of the claimed composition, it is now possible to provide tablets with a higher content of omega-3 fatty acids. When using omega-3 fatty acid amino acid salts, which have been prepared from sufficiently highly concentrated EPA or DHA starting materials or EPA/DHA mixtures, the resulting tablets may have a content of omega-3 fatty acids of over 40% in total. In the case of such high omega-3 fatty acid contents, the intake of only a few tablets per day is sufficient, possibly only one single tablet per day, in order to reach the recommended daily intake amount of omega-3 fatty acids.

Therefore, in an advantageous configuration of the present invention, the content of omega-3 fatty acids is in total 40% by weight or more, preferably 50% by weight or more, based on the total weight of the composition.

Particularly surprising was the finding that omega-3 fatty acid amino acid salts with addition of only a substance, which forms an eutectic system with the omega-3 fatty acid amino acid salt and acting as a plasticizer and thereby lowering the glass transition temperature to below 110° C., can directly be compressed to tablets. Finally, the preparation of tablets by direct compression has generally been described only for a few substances such as calcium sulphate, calcium hydrogen phosphate, (microcrystalline) cellulose, lactose or other sugar and sugar derivatives, but not for omega-3 fatty acids or derivatives thereof (Pharmazeutische Hilfsstoffe [Pharmaceutical Auxiliaries], Peter C. Schmidt, Siegfried Lang, p. 131f., GOVI-Verlag, ISBN 978-3-7741-1222-3).

Omega-3 fatty acids, which may be used individually or in any combination in the method according to the invention, comprise for example α-linolenic acid (ALA) 18:3 (n-3) (cis,cis,cis-9,12,15-octadecatrienoic acid), stearidonic acid (SDA) 18:4 (n-3) (all-cis-6,9,12,15,-octadecatetraenoic acid), eicosatrienoic acid (ETE) 20:3 (n-3) (all-cis-11,14,17-eicosatrienoic acid), eicosatetraenoic acid (ETA) 20:4 (n-3) (all-cis-8,11,14,17-eicosatetraenoic acid), heneicosapentaenoic acid (HPA) 21:5 (n-3) (all-cis-6,9,12,15,18-heneicosapentaenoic acid), docosapentaenoic acid (clupanodonic acid) (DPA) 22:5 (n-3) (all-cis-7,10,13,16,19-docosapentaenoic acid, tetracosapentaenoic acid 24:5 (n-3) (all-cis-9,12,15,18,21-tetracosapentaenoic acid), tetracosahexaenoic acid (nisinic acid) 24:6 (n-3) (all-cis-6,9,12,15,18,21-tetracosahexaenoic acid).

Polyunsaturated omega-3 fatty acids, which may be used for producing the tablets according to the invention, may be obtained from any suitable starting material, which may in addition be processed with any suitable method. Typical starting materials include all parts of fish carcasses, vegetables and other plants, and also material from microbial fermentation or fermentation of algae. Typical processing methods for such starting materials are, inter alia, steps for crude oil extraction, such as extraction and separation of the starting materials and also steps for refining crude oils, such as deposition and degumming, deacidification, bleaching and deodorant (cf. e.g. "EFSA Scientific Opinion on Fish Oil for Human Consumption"). It is advantageous to use different plant oils as starting material, such as linseed oil, algal oil, hemp seed oil, rapeseed oil, borage seed oil, flaxseed oil, canola oil, soybean oil. Further processing methods include, inter alia, steps for the at least partial conversion of omega-3 fatty acid esters to the corresponding free omega-3 fatty acids or inorganic salts thereof.

In a further preferred embodiment of the present invention, the source for omega-3 fatty acids is chosen from at least one of the following: fish oil, squid oil, krill oil, linseed oil, borage seed oil, algal oil, hemp seed oil, rapeseed oil, flaxseed oil, canola oil, soybean oil.

Omega-3 fatty acids may also be obtained by cleaving the omega-3 fatty acid esters and subsequent removal of the thereby released alcohols from the compositions, which consist principally of omega-3 fatty acid esters. The ester cleavage is preferably carried out under basic conditions. Methods for ester cleavage are well known from the prior art.

In the context of the present invention, preferred omega-3 fatty acids to be used are eicosapentaenoic acid ("EPA") and docosahexaenoic acid ("DHA"). It is further preferred to use a mixture of eicosapentaenoic acid ("EPA") and docosahexaenoic acid ("DHA").

The stability of a tablet according to the invention is not dependent on whether the fatty acid component is, for example, a hydrolysate of an EPA or DHA concentrate, of an EPA/DHA semi-concentrate or even a fish oil.

In an advantageous configuration of the present invention, the omega-3 fatty acids are selected from eicosapentaenoic acid (EPA), docosahexaenoic acid (DHA) and mixtures of the same.

In an advantageous configuration, the tablet further comprises one or more additional active ingredients selected from anthocyanins, vitamins, minerals, fiber, fatty acids, amino acids and proteins.

The salts of omega-3 fatty acids and amino acids are dissolved in the digestive tract, wherein the free omega-3 fatty acids are released which are suitable for direct absorption by the body, and prior chemical or enzymatic cleavage is no longer required, such as is the case in the omega-3 triglycerides in fish oil or the omega-3 fatty acid ethyl esters prepared therefrom. By coating the tablet with an enteric coating, the omega-3 fatty acids are only released in the small intestine, which demonstrably is the actual location in the body for the absorption of fatty acids from the digestive tract, such that the omega-3 fatty acids are available for immediate absorption in the preferred free form. The effects such as reflux or unpleasant fishy regurgitation often usually linked with the release of omega-3 fatty acid oils in the stomach is thus avoided.

In an advantageous configuration of the present invention, the tablet according to the invention is completely coated with a layer of a polymer selected from the group consisting of poly(meth)acrylate, alginate, hypromellose acetate succinate (HPMCAS), shellac and combinations thereof.

In a further advantageous configuration of the present invention, the tablet according to the invention is completely coated with a substance, which is suitable to release less than 10% by weight of the content of omega-3 fatty acid amino acid salt when the tablet is dipped completely in 0.1N hydrochloric acid for a period of 2 hours.

In order to achieve a disintegration of the tablet in the digestive tract, disintegrants are added to the composition, which expand and dissolve when wet causing the tablet to break apart in the digestive tract, releasing the active ingredients for absorption. They ensure that when the tablet is in contact with water, it rapidly breaks down into smaller fragments, facilitating dissolution.

In a further aspect, the present invention relates to a method for preparing a tablet according to the invention, characterized in that the omega-3 fatty acid amino acid salts are compressed, optionally together with one or more binders and/or one or more structure-forming substances.

In a preferred configuration, the method according to the invention is characterized in that the omega-3 fatty acid amino acid salts are compacted prior to the compression. The compaction can be accomplished, for example, using an Exzenter tablet press with 25 mm biplanar punches at a compression force of 15-20 kN (30.5-40.7 MPa). The resulting product can subsequently be crumbled again via a 1 mm sieve.

In a further preferred configuration, the method according to the invention is characterized in that the omega-3 fatty acid amino acid salts are granulated preferably with a solvent, for example water or ethanol, or with a solvent mixture, for example a water/ethanol mixture, prior to the compression and optionally prior to the compaction.

Omega-3 fatty acid amino acid salts are known in principle. As described at the outset, these may be obtained as fine, virtually colourless powders by precipitation from aqueous or aqueous alcoholic media or by spray-drying, which differ advantageously from the waxy consistency of these substances described hitherto.

In a preferred configuration, the method according to the invention is characterized in that the omega-3 fatty acid amino acid salts are obtained by precipitation from aqueous or alcoholic aqueous solution.

In a further preferred configuration, the method according to the invention is characterized in that the omega-3 fatty acid amino acid salts are obtained by spray-drying of an aqueous or alcoholic aqueous solution.

In a further aspect, the present invention relates to the use of a tablet according to the invention as a food supplement or pharmaceutical product.

In the context of the present invention, pharmaceutical products may comprise, in addition to the omega-3 fatty acids described here, both pharmaceutically acceptable auxiliaries and pharmaceutical active ingredients such as statins, anti-hypertensive agents, antidiabetics, antidementia agents, antidepressants, anti-obesity agents, appetite suppressants and agents to improve memory and/or cognitive function.

In a further aspect, the present invention relates to a mixture of omega-3 lysine salt and a plasticizer that depicts a change in color when compressed to a tablet, wherein the rate in change of color is dependent on the amount of plasticizer and the rate of change from insufficiently plasticized to compressible changes by a factor of 0.57 or smaller, preferably by a factor of 0.3 or smaller.

The present invention is described in detail by means of the following non-limiting experiments.

Example 1: Analysis of Glass Transition Temperature (Tg) of Mixtures

TABLE 1

Analysis of glass transition temperature of different mixtures of Omega-3-lysine salts with Magnesium stearate (Mg-stearate) and Stearic acid (n.d. = not detectable)

| Omega 3-Lysine-salt [weight-%] | Mg-Stearate [weight-%] | Stearic Acid [weight-%] | Melting Peak [mJ] | Glass Transition Temperature [° C.] |
|---|---|---|---|---|
| 100.0 | 0.0 | 0.0 | 83.79 | 146.4 |
| 70.0 | 30.0 | 0.0 | 173.52 | 62.45 |
| 69.9 | 0.0 | 30.1 | 194.3 | 60.68 |
| 85.0 | 15.0 | 0.0 | 37.59 | 43.39 |
| 85.0 | 0.0 | 15.0 | 92.11 | 38.85 |
| 70.0 | 15.0 | 15.0 | 252.52 | 61.73 |
| 90.0 | 5.0 | 5.0 | 41.44 | 33.39 |
| 74.7 | 20.0 | 5.3 | 146.13 | 56.64 |
| 74.9 | 5.0 | 20.1 | 179.57 | 59.63 |
| 79.9 | 10.0 | 10.1 | 137.52 | 51.8 |
| 80.0 | 10.0 | 10.0 | 124.66 | 53.63 |
| 79.8 | 10.0 | 10.2 | 164.6 | 54.47 |
| 90.0 | 10.0 | 0.0 | — | 35.57 |
| 95.0 | 5.0 | 0.0 | 0.0 | n.d. |
| 97.0 | 3.0 | 0.0 | 0.0 | n.d. |
| 98.0 | 2.0 | 0.0 | 0.0 | n.d. |
| 92.5 | 3.75 | 3.75 | — | 28.8 |
| 92.5 | 7.5 | 0.0 | 0.0 | 25.22 |
| 92.5 | 0.0 | 7.5 | 0.0 | n.d. |
| 85.0 | 7.5 | 7.5 | 85.46 | 44.38 |
| 90.0 | 5.0 | 5.0 | 0.0 | n.d. |
| 90.0 | 5.0 | 5.0 | 0.0 | n.d. |
| 95.0 | 2.5 | 2.5 | 0.0 | n.d. |
| 97.0 | 1.5 | 1.5 | 0.0 | n.d. |
| 97.5 | 1.2 | 1.3 | 0.0 | n.d. |

300 g of the mixture were added into a 1l powder flask and mixed manually for about 2 minutes. The melting peak and glass transition temperature were measured using differential scanning calorimetry (DSC), which was performed according to DIN-ISO_11357-2.

Both magnesium stearate and stearic acid worked well as plasticizer and lead to a reduction of the glass transition temperature below 100° C. In these experiments, the glass transition temperature could even be reduced to values below 65° C.

The compositions with a glass transition temperature below 100° C. could easily directly be compressed (45-60 MPa) to tablets and resulted in soft (55-70N) but elastic tablets.

When using magnesium stearate and stearic acid as plasticizer, it is possible to compress tablets with a maximal content of 95% omega-3 fatty acid lysine salt.

The melting peak values confirmed that no conversion of the salts took place. However, for the measurements with less than 7.5% of plasticizer, no melting peak could be detected with the DSC measurements. The disappearing of the melting peak shows the lower determination limit. The equipment is not capable of determining a melting peak below a content of plasticizer of 7.5% in the mixture, but can still detect the change in DSC of the entire system. Therefore, an alternative detection method was needed.

The magnitude of the effect in the DSC makes it beneficial to describe the observed effect with other methods. A change in color during compression can be observed with the naked eye, when tablets are placed on a uniform background (e.g. sheet of paper). This observation can be quantified by image analysis. Moreover, a state of the art tablet press keep track of punch position and applied force during compression.

Example 2: Analysis of Force-Path Data

In order to determine the lower limit of plasticizer content for the compositions according to the present invention, force-path data were analyzed. From these force-path diagrams, the work, which is needed, can be calculated and divided into friction, deformation and elastic relaxation.

The observed eutectic behavior also results in softening of the mixture and should therefore be detectable by a reduction of the work related to friction and an increase of deformation, as the effect starts to become present. When the mixture is further plasticized (drop of Tg), the elastic behavior is increased, so the work for deformation should drop and the elastic relaxation should increase.

For the analysis, the Omega 3-lysine-salt was mixed with different amounts of Magnesium-stearate as shown in Example 1. To obtain reproducible results, 0.5% w/w of Silica was added to the mixtures. This ensures flowability and even filling of the dye. The work divided into friction, deformation and elastic relaxation is depicted in FIG. 1. FIG. 1 shows the work during compression. The Mg-stearate content (referring to Omega-3-lysine salt) in % w/w is depicted on the x-axis and the portions of work friction, plastic deformation and elastic relaxation in % are depicted on the y-axis.

As shown in FIG. 1, the work to compress a tablet shows no effect between 0 and 2% w/w Mg-stearate in Omega 3-lysine salt. Already at 2.5% w/w of Mg-stearate, a significant step down in friction and an increase in plastic deformation takes place and the mixture becomes compressible. A further increase in Mg-stearate leads to a decrease of plastic deformation and an increase elastic relaxation.

This data was generated from compression of Omega 3-lysine salt-Mg-stearate mixtures on a Korsch XP1 eccentric tablet press, equipped with a round, biplane punch of 25 mm in diameter at a speed of 20 tablets per minute. The filling depth was 8.5 mm, and the applied compression force of 22 kN resulted in a pressure of 44.8 MPa.

Data was recorded using Pharma Research software from Korsch and analyzed using the Software "Extended Data analysis" from Korsch.

Example 3: Evaluation of Change in Color

When compressing a powder blend of Omega 3-lysine-salt and Mg-stearate on a press, two things happen simultaneously: With an increase of Mg-stearate, the entire mixture moves to white (=increase in RGB-product using the RGB color space) and the number of boundary surfaces decreases as the material is compressed. Existing cavities/fissures disappear, which leads to less diffraction and thereby an increase of the intensity of existing color.

Thus, to properly describe the change in material behavior, a 3-dimensional space of color, amount of Mg-stearate in the mixture and pressure has to be utilized.

The following data set was created using the same equipment setup as mentioned before. In the recipe, 1% w/w Silica was added, as flowability was not entirely sufficient in trials before. As omega 3-lysine-salt has a salmon like, reddish color, the red part of RGB color space was used.

To obtain the RGB-values for each mixture and pressure, four compacted samples were scanned (reflected light, 300 dpi, 24 bit, Adobe RGB) in front of a black background. On this a flatbed scanner Epson V850 Pro (Software: Epson Scan Ver. 3.9.3) with the possibility to define every acquisition parameter as well as the RGB color space and the loss-free file format "TIF" was used. That leads to evaluable images with 8 bit color intensity information for each color (red, green, blue=RGB). This results in numerical values from 0 to 255. For each compacted sample, an area of interest was defined and the mean color was determined using the software Image Pro Plus (Ver. 7.01). The area of interest (A01) was the largest possible circle on the compacted sample without any mechanical defects (e.g. chipped edge). For every sample at least four A01 (each diameter: 23 mm/area: 415 mm$^2$) were averaged to appraise the color values. The red color amount increases for red samples. The red color value increases with red samples, while the blue and green values decrease (and vice versa). The scanning system was checked with a black background and a white-reference to ensure the functionality. The black sample (background) has RGB values below 30 (for each color); a white-reference is above 240. Every colored samples is in between this limits. By multiplying the color values (RGB product, 3*8 bit=24 bit) the brightness can be rated and compared.

The following data was obtained.

TABLE 2

RGB values for different mixtures of Omega-3-lysine salt and Mg-stearate

| Mg-stearate in Omega-3-Lysine salt [% w/w] | Pressure [MPa] | Red [8 bit] | RGB product [24 bit] |
|---|---|---|---|
| 0 | 26.77 | 178 | 1.47972e+006 |
| 0 | 37.85 | 164 | 1.04747e+006 |
| 0 | 44.68 | 159 | 1.03146e+006 |
| 2 | 25.46 | 196 | 2.72342e+006 |
| 2 | 39.05 | 190 | 2.20448e+006 |
| 2 | 49.85 | 181 | 1.87307e+006 |
| 3 | 26.10 | 200 | 3.05369e+006 |
| 3 | 33.23 | 191 | 2.40717e+006 |
| 3 | 50.36 | 190 | 2.47523e+006 |
| 5 | 29.13 | 204 | 3.6863e+006 |
| 5 | 33.96 | 203 | 3.60747e+006 |
| 5 | 45.02 | 198 | 3.21602e+006 |

Once the mixture is sufficiently plasticized, a significant effect of Mg-stearate on the red color can be observed, i.e. the color becomes less intense.

By fitting a surface through the data points of each plain the following regression models are obtained using Modde from Umetrics AB (Version 9.1.1):

| Red | Effect | Conf. int(±) | RGB Product | Effect | Conf. int(±) |
|---|---|---|---|---|---|
| Mg-stearate | 35.143 | 5.75075 | Mg-stearate | 2.29632e+006 | 259768 |
| Mg-stearate^2 | −15.8219 | 8.41814 | Pressure | −600894 | 255815 |
| Pressure | −13.1153 | 5.51053 | Pressure^2 | 492668 | 443818 |
| Mg-st*Pressure | 9.02263 | 9.27609 | | | |
| | Q2= | 0.930 | | Q2= | 0.967 |
| | R2= | 0.974 | | R2= | 0.983 |
| | Conf. lev.= | 0.95 | | Conf. lev.= | 0.95 |

FIG. 2 shows the curves for the measured red-values for different Mg-stearate contents (FIG. 2a) and the RGB-products for the different Mg-stearate contents (FIG. 2b) during compression. As expected, the RGB-product behaves practically linear to the Mg-stearate content, like also shown in the main effect (compare FIG. 2b).

On the contrary, the Mg-stearate effect on the red color is not linear. As depicted in FIG. 2a, there is only a very small change in slope between 0 and 2%, respectively 1 and 3%

Mg-stearate, but a drastic change in slope between 3 and 5% Mg-stearate. Thus, the onset of the improved compression is between 2 and 3% Mg-stearate in relation to omega-3-lysine salt. The corresponding slopes are depicted in FIG. 2c, which clearly shows the intersection point at around 2,5% Mg-stearate. The difference between the slopes is 6.83 to 11.9, corresponding to a factor of 0.57. In this case, the rate in change of color is dependent on the amount of plasticizer and the rate of change from insufficiently plasticized to compressible changes by a factor of 0.57

Example 4

Tablets with different amounts of omega-3 fatty acid salts were prepared. A tablet could be prepared, which contains 50.00% by weight of omega-3 fatty acid lysine salt. The amount of magnesium stearate used corresponds to 5% by weight based on the amount of salt.

| Material | Amount [% by weight] |
| --- | --- |
| Omega-3 fatty acid lysine salt (EPA-lysinate) | 50.00 |
| Magnesium stearate | 2.50 |
| Compactrol | 23.81 |
| C* Pharmagel | 22.69 |
| Aerosil 200 (highly dispersed silicon dioxide) | 1.00 |
| Sum total | 100.00 |

For all examples, omega-3 fatty acid lysine salt was mixed with the other components using a tumbling mixer (Turbula T-10, Willy A. Bachofen AG).

In all examples, the formulas could be compressed with 21×9 mm oblong punches with a target mass of 800 mg using single punch tablet press machine XP1, Korsch. Dissolution/disintegration was tested in buffer at pH 6.8 in a disintegration tester (PTZ Auto 4 EZ, Pharma Test Apparatebau AG). The disintegration time was under 1 h.

In summary, tableting was possible both on rotary and eccentric press with a relatively low pressure, which was unexpected and showed how good the compositions stick together, when using only small amounts of magnesium stearate) as plasticizer.

Example 5

A tablet containing 50.00% by weight of omega-3 fatty acid lysine salt was prepared, with a content of magnesium stearate corresponding to 5% by weight based on the amount of omega-3 fatty acid lysine salt.

| Material | Amount [% by weight] |
| --- | --- |
| Omega-3 fatty acid lysine salt (EPA-lysinate) | 50.00 |
| Magnesium stearate | 2.50 |
| Prosolv EASYtab NUTRA | 44.50 |
| Aerosil 200 (highly dispersed silicon dioxide) | 1.00 |
| Croscarmellose sodium (Ac-Di-Sol) | 2.00 |
| Sum total | 100.00 |

Disintegration time was analyzed in buffer at pH 6.8 and was 7:38 min at a 3 kN compaction force and around 45 min at a 5 kN compaction force.

Example 6

A tablet containing 40.00% by weight of omega-3 fatty acid lysine salt was prepared, with a content of magnesium stearate corresponding to 6.25% by weight based on the amount of omega-3 fatty acid lysine salt.

| Material | Amount [% by weight] |
| --- | --- |
| Omega-3 fatty acid lysine salt (EPA-lysinate) | 40.00 |
| Magnesium stearate | 2.50 |
| Prosolv EASYtab NUTRA | 54.50 |
| Aerosil 200 (highly dispersed silicon dioxide) | 1.00 |
| Croscarmellose sodium (Ac-Di-Sol) | 2.00 |
| Sum total | 100.00 |

The disintegration time was analyzed in buffer at pH 6.8 and was under 1 h at a 3 kN compaction force and at a 5 kN compaction force. Analysis of disintegration time in FeSSIF was determined to be ~15 min at a 3 kN compaction force and ~15-10 min at a 5 kN compaction force.

Example 7

A tablet containing 40.00% by weight of omega-3 fatty acid lysine salt was prepared, with a content of magnesium stearate corresponding to 6.25% by weight based on the amount of omega-3 fatty acid lysine salt.

| Material | Amount [% by weight] |
| --- | --- |
| Omega-3 fatty acid lysine salt (EPA-lysinate) | 40.00 |
| Magnesium stearate | 2.50 |
| MCC102 | 27.50 |
| DCPD | 27.50 |
| Aerosil 200 (highly dispersed silicon dioxide) | 0.50 |
| Vivasol GM LF | 2.00 |
| Sum total | 100.00 |

The disintegration time was analyzed in buffer at pH 6.8 and was ~26 min at a 5 kN compaction force. The tablet hardness was determined to be 76.8 N.

The invention claimed is:

1. A tablet, comprising a composition comprising at least one omega-3 fatty acid amino acid salt and at least one substance which forms an eutectic system with the at least one omega-3 fatty acid amino acid salt and thereby acts as a plasticizer,
    wherein the amino acid in the at least one omega-3 fatty amino acid amino acid salt is a basic amino acid,
    the composition has a glass transition temperature Tg of less than 110° C., and
    the composition is compressed to form the tablet.

2. The tablet according to claim 1, wherein a content of the plasticizer is at least 2% by weight, based on a total amount of omega-3 fatty acid amino acid salts in the composition.

3. The tablet according to claim 1, wherein the plasticizer is selected from the group consisting of fatty acids, fatty acid salts, fatty acid esters and polyethylene glycol.

4. The tablet according to claim 1, wherein a content of omega-3 fatty acids is in total 40% by weight or more, based on a total weight of the composition.

5. The tablet according to claim 1, wherein a source for the at least one omega-3 fatty acid is at least one selected from the group consisting of fish oil, squid oil, krill oil, linseed oil, borage seed oil, algal oil, hemp seed oil, rapeseed oil, flaxseed oil, canola oil, and soybean oil.

6. The tablet according to claim 1, wherein the at least one omega-3 fatty acid is selected from the group consisting of eicosapentaenoic acid (EPA), docosahexaenoic acid (DHA) and mixtures thereof.

7. The tablet according to claim 1, further comprising at least one additional active ingredient selected from the group consisting of anthocyanins, vitamins, minerals, fiber, fatty acids, amino acids and proteins.

8. The tablet according to claim 1, wherein the composition is completely coated with a layer of a polymer selected from the group consisting of poly(meth)acrylate, alginate, hypromellose acetate succinate (HPMCAS), shellac, pectin and combinations thereof.

9. The tablet according to claim 1, wherein the tablet is completely coated with a substance which is suitable to release less than 10% by weight of the content of omega-3 fatty acid amino acid salt when the tablet is dipped completely in 0.1N hydrochloric acid for a period of 2 hours.

10. A method for preparing the tablet according to claim 1, comprising:
    compressing the omega-3 fatty acid amino acid salts, optionally together with one or more binders and/or one or more structure-forming substances.

11. The method according to claim 10, wherein the omega-3 fatty acid amino acid salts are compacted prior to the compression.

12. The method according to claim 10, wherein the omega-3 fatty acid amino acid salts are granulated with a solvent or solvent mixture prior to the compression and optionally prior to compaction.

13. The method according to claim 10, wherein the omega-3 fatty acid amino acid salts are obtained by precipitation from aqueous or alcoholic aqueous solution.

14. The method according to claim 10, wherein the omega-3 fatty acid amino acid salts are obtained by spray-drying of an aqueous or alcoholic aqueous solution.

15. A food supplement or a pharmaceutical product, comprising the tablet according to claim 1.

16. The tablet according to claim 1, wherein the composition is completely coated with an enteric coating.

17. The tablet according to claim 1, wherein the plasticizer is selected from the group consisting of magnesium stearate and stearic acid, and a content of the plasticizer is at least 2.5% by weight, based on the total amount of omega-3 fatty acid amino acid salts in the composition.

18. The tablet according to claim 1,
    wherein the composition further comprises at least one plasticizer selected from the group consisting of magnesium stearate and stearic acid,
    the omega-3 fatty acids are selected from the group consisting of eicosapentaenoic acid (EPA), docosahexaenoic acid (DHA) and mixtures thereof, and
    the basic amino acids are selected from the group consisting of lysine, arginine, ornithine, histidine, and citrulline.

19. A tablet, comprising a composition comprising at least one omega-3 fatty acid amino acid salt,
    wherein the amino acid in the at least one omega-3 fatty amino acid amino acid salt is a basic amino acid,
    the composition has a glass transition temperature Tg of less than 110° C., and
    the tablet is completely coated with a substance which is suitable to release less than 10% by weight of the content of omega-3 fatty acid amino acid salt when the tablet is dipped completely in 0.1N hydrochloric acid for a period of 2 hours.

* * * * *